United States Patent
Pak

(10) Patent No.: US 6,726,939 B1
(45) Date of Patent: Apr. 27, 2004

(54) COMPOSITION AND METHOD FOR REDUCING BLOOD PRESSURE, ALLEVIATING OR ELIMINATING ANGINA PECTORIS AND HEADACHES, AND ENHANCING SKIN AND HAIR

(76) Inventor: Kyoungsik Pak, 371 Sweetbriar Rd., King of Prussia, PA (US) 19406

( * ) Notice: Subject to any disclaimer, the term of this patent is extended or adjusted under 35 U.S.C. 154(b) by 0 days.

(21) Appl. No.: 09/533,420

(22) Filed: Mar. 22, 2000

(51) Int. Cl.$^7$ ............................................. A61K 35/78
(52) U.S. Cl. ...................................... 424/729; 424/725
(58) Field of Search ............................... 424/195.1, 729, 424/725, 70.51; 426/597; 514/52, 597

(56) References Cited

U.S. PATENT DOCUMENTS

| | | | |
|---|---|---|---|
| 5,053,429 A | 10/1991 | Hirsch et al. | |
| 5,703,127 A | 12/1997 | Pak | |
| 5,906,811 A | * 5/1999 | Hersh | ......................... 424/54 |
| 5,952,367 A | 9/1999 | Pak | |

FOREIGN PATENT DOCUMENTS

WO  WO 95/33486  12/1995

OTHER PUBLICATIONS

*The Pharmacology of Chinese Herbs*, by Kee Chang Huang, pp. 167–169.
*Biochemistry*, Second Edition, published by Worth Publishers, Inc., pp. 126, 272–273 and 697–699.
*Chinese Herbal Remedies*, by Albert Y. Leung, pp. 156–159.
*Remington's Practice of Pharmacy*, Ninth Edition, published by The Mack Publishing Company, pp. 846–851 and 908.
*Sulphydryl–Containing Agents: A New Approach to the Problem of Refractory Peptic Ulceration*, by Aws S. Salim, pp. 301–306.
*The Nutrition Desk Reference*, published by Keats Publishing, Inc., p. 76.
*The Doctors' Vitamin and Mineral Encyclopedia*, published by Simon and Schuster, pp. 224–225.
An Advertisedment in the Feb. 19, 1999 Philadelphia Inquirer by Douglas Huntt, M.D. titled, "New Researxhy Pinpoints Antioxitdents That Fight 50 Diseases".
An Article in the Nov. 12, 1998 Courier–Post titled, "The appleal of green tea: Tastes great, less cell damage".
*National Formulary III*, published by the American Pharmaceutical Association, pp. 434–437.
*Physician's Desk Reference*, published by Medical Economies, Inc., p. 533.
*Physician's Desk Reference*, published by Medial Economies, Inc., p. 526.
*The United States Pharmacopiea*, published by United States Pharmacopiea Convention, Inc., pp. 342–343.
*The United States Pharmacopiea*, published by the United States Pharmacopiea Convention, Inc., p. 506.

*The Merck Index Eleventh Edition*, p. 1581.
*USPXX* (re: Methionine), one page.
*The Merck Index Ninth Edition*, one page (re: Methionine).
*Modern Nutirition in Health and Disease*, editied by Maurice E. Shils & Vernon R. Young, pp. 1363–1365.
*Gastrointestinal Health*, by Steven R. Peikin, pp. 44–45.
*Physician's Gen RX–The Complete Drug Reference*, p. II–1276.
*Nutirition Desk Refernce*, by Robert H. Garrison, Jr., M.A.R. PH., & Elizabeth Somer, M.A., pp. 13 and 22.
*The Doctor's Vitamin and Mineral Encyclopedia*, by Sheldon Saul Handler, M.D. Ph.D., pp. 224–225.
*National Formulary XIII*, published by the American Pharmaceutical Association, pp. 320–321.
*Physician's Desk Reference*, published by Reid Laboratories, Inc., p. 770.
*USPXX* (re: Fructose), one page.
*Chinese Herbal Remedies*, by Albert V. Leung, pp. 156–159.
*Remington's Practice of Pharmacy*, Ninth Edition, published by The Mack Publishing Company, pp. 846–851 and 908.
*Sulphydryl–Containing Agents: A New Approach to the Problem of Refractory Peptic Ulceration* by Aws S. Salim, pp. 301–306.
*The Nutrition Desk Reference*, published by Keats Publishing, Inc., p. 76.
The Doctors' Vitamin and Mineral Encyclopedia.
HCA Plus Absgtract 1970: 41562, Gasparini (1969).
HCA Plus Abstract 1996: 147790, Riga, D. et al (1995).
DiPiro, et al. "Pharmacotherapy: A Pathosysiologic Approach", Elsevier Science, New York, 1989, p. 20.
*The Merck Index Eleventh Edition*, Susan Budavar, editor, p. 1581, (1989).
*Physician's Desk Reference*, published by Reid Laboratories, Inc., p. 770, (1962).
HCAPLUS Abstract 1970: 41562, Gasparini (1969).
HCAPLUS Abstract 1996: 147790, Riga, D. et al (1995).
DiPiro, et al . "Pharmacotherapy: A Pathosysiological Approach", Elsevier Science, New York, p. 20, (1989).
*The Pharmacology of Chinese Herbs*, by Kee Chang Huang, pp. 167–169, ( 1993).
*Biochemisty*, 2nd Ed., by Albert L. Lehninger, Worth Publishers, Inc., pp. 697–699 and p. 126 and pp. 272–273, (1975).
*The Merck Index Ninth Edition*, one page (re:Methionine), Martha Winholz, editor, p. 780, ( 1976).

(List continued on next page.)

*Primary Examiner*—Jon P. Weber
*Assistant Examiner*—Patricia A Patten
(74) *Attorney, Agent, or Firm*—John F. A. Earley; John F. A. Earley, III; Harding, Earley, Follmer & Frailey

(57) ABSTRACT

A composition for reducing or stabilizing blood pressure and relieving headaches comprises (a) a first component comprising (i) tea, or (ii) tea and vitamin B6, or (iii) a combination of vitamin C and vitamin B6, or (iv) a combination of tea, vitamin C, and vitamin B6, and (b) a sulfur-containing amino acid. Preferably, the composition is provided in tablet or capsule form.

30 Claims, No Drawings-

OTHER PUBLICATIONS

*Modern Nutrtion in Health and Disease*, edition by Maurice E. Shils & Vernon R. Young, pp. 1363–1366, (1986).
*Gastrointestinal Health*, by Steven R. Peiken, pp. 44–45, (1991).
*Physician's Gen RX–The Complete Drug Reference*, Philip J. Denniston, Jr., editor in chief, pp. II–1276, (1995).
*Nutrition Desk Reference*, by Robert H. Garrison, Jr., M.A.R. PH., & Elizabeth Somer, M.A., pp. 13 and 22, (1985).
*Nationl Formulary XIII*, published by the American Pharmaceutical Association, pp. 320–321, (Sep. 1, 1970).
Associated Press article in the Jan. 6, 2000 *Philadelphia Inquirer* titled "FDA Gives Dietary Supplements New Leeway".
*Chinese Herbal Remedies*, by Albert Y. Leung, pp. 156–159, (1984).
*Remington's Practice of Pharmacy*, Ninth Edition, published by The Mack Publishing Company, pp. 846–851 and 908, (1948).
*Sulphydryl–Containing Agents: A New Approach to the Problem of Refractory Peptic Ulceration* by Aws S. Salim, Pharmacology 1992; 45: 301–306.
*The Nutrition Desk Reference* by Robert H. Garrison, Jr., published by Keats Publishing, Inc., p. 76, (1985).

*The Doctors' Vitamin and Mineral Encyclopedia*, published by Simon and Schuster, pp. 224–225. by Sheldon Saul Handler, M.D. PhD. (1990).
An Advertisement in the Feb. 19, 1999 *Philadelphia Inquirer* by Douglas Hunt, M.D. titled, "New Research Pinpoints Antioxidents That Fight 50 Diseases".
An Associated Press article in the Nov. 12, 1998 *Courier–Post* titled, "The appeal of green tea: Tastes great, less cell damage".
*National Formulary III*, published by American Pharmaceitical Association, pp. 434–437 (Sep. 1, 1970).
*Physicians'Desk Reference to Pharmaceutical Specialties and Biologicals*, published by Medical Economics, Inc., p. 533 (1965).
*Physician's Desk Reference to Pharmaceuticals Specialties and Biologicals*, published by Medical Econonmics, Inc., p. 526, (1965).
*The United States Pharmacopiea/The National Formulary*, published by United States Pharmacopiea Convention, Inc., pp. 342–343, (1980).
*The United States Pharmacopiea/The National Formulary*, published by the United States Pharmacopiea Convention, Inc. p.506, (Jul. 1, 1980).

* cited by examiner

COMPOSITION AND METHOD FOR REDUCING BLOOD PRESSURE, ALLEVIATING OR ELIMINATING ANGINA PECTORIS AND HEADACHES, AND ENHANCING SKIN AND HAIR

BACKGROUND OF THE INVENTION

1. Field of the Invention

This invention relates to the field of blood pressure and angina pectoris, and specifically is concerned with a composition for stabilizing or reducing blood pressure and alleviating or preventing angina pectoris.

2. Description of the Prior Art

Teas, especially green tea, oolong tea, and black tea, have come to be recognized for their advantageous properties for enhancing health and longevity.

Green tea, for example, contains antioxidants, including antioxidant polyphenols that have been linked with providing antiviral, antibacterial, and anticarcinogenic properties, as well as stimulating the immune system. Further, it is thought that green tea may assist in the fight against aging, with the antioxidants in green tea preventing or blocking the formation of free radicals in the human body. Additionally, it is thought that green tea may help relieve headaches, including migraine headaches, eliminate or relieve angina pectoris, lower overall cholesterol levels, reduce the risk of heart attacks, lessen the likelihood of death from heart attack, decrease the risk of stroke, enhance immune functions, and aid digestion.

However, many people incur undesirable side effects of tea, such as insomnia, dizziness, heart palpitations, excessive urination, upset stomach, stomach pain, nausea, vomiting, and constipation. Due to such undesirable side effects, some people must refrain from ingesting tea, thereby missing out on the advantageous properties provided from tea.

Sulfur-containing amino acids, such as methionine, are known in human beings to repair damaged cells of skin, nails, and hair, to help prevent disorders of mucus membranes, to help relieve nervousness, and to help prevent disorders of the nervous system. Methionine also is known to regulate body metabolism.

SUMMARY OF THE INVENTION

It is an object of the invention to provide a composition that stabilizes or reduces blood pressure.

It is another object of the invention to provide a composition that eliminates or relieves angina pectoris.

It is another object of the invention to provide a composition that helps relieve migraine headaches.

It is another object of the invention to provide a composition that delays the wrinking of skin and strengthens and darkens hair.

It is another object of the invention to provide a composition that provides advantageous properties of tea, but at the same time reduces or eliminates unwanted and undesirable side effects of tea such as insomnia, dizziness, heart palpitations, excessive urination, upset stomach, stomach pain, nausea, vomiting, and constipation.

Another object of the invention is to provide a method of providing to human beings the advantageous properties associated with tea, but at the same time reduces or eliminates unwanted and undesirable side effects of tea such as insomnia, dizziness, heart palpitations, excessive urination, upset stomach, stomach pain, nausea, vomiting, and constipation.

These and other objects of the invention are accomplished by my invention, which is described below.

DETAILED DESCRIPTION OF THE INVENTION

In accordance with the invention, my inventive composition for reducing or stabilizing blood pressure comprises (1) tea, or tea and vitamin B6, or the combination of vitamin C and vitamin B6, or the combination of tea, vitamin C, and vitamin B6, and (2) a sulfur-containing amino acid.

In a preferred embodiment of the invention, the composition provides advantageous properties of tea, such as those mentioned above, but at the same time reduces or eliminates unwanted side effects associated with tea, such as headaches, insomnia, dizziness, heart palpitations, excessive urination, stomach upset, stomach pain, nausea, vomiting, and constipation, comprises tea and a sulfur-containing amino acid. In particular, some embodiments of the invention which contain tea have been observed to provide the benefit of alleviating or preventing angina pectoris and headaches.

Preferably, the composition is provided in tablet form, having been made by combining the components of the composition together in powder form, granular form, or the like, and then tableted. The tablets may be provided with coatings used to coat pharmaceutical tablets, vitamin tablets, and the like, if desired. Alternatively, the powder/granular composition, in accordance with the invention, may be provided in capsule form.

The invention also includes a method for reducing or stabilizing blood pressure which comprises the steps of providing (1) an effective dosage of (i) tea, or (ii) tea and vitamin B6, or (iii) a combination of a vitamin C and vitamin B6, or (iv) the combination of tea, vitamin C, and vitamin B6, and (2) an effective dosage of a sulfur-containing amino acid, and orally ingesting the effective dosages, wherein the ingested effective dosages result in providing advantageous properties such as reducing or stabilizing blood pressure. When the inventive method includes an effective dosage of tea in certain ranges, the additional benefit of alleviating or preventing angina pectoris and headaches has been observed. The benefits of improving the health and appearance of skin and hair are also achieved with the present method.

Further, the invention also includes a method of providing advantageous properties associated with tea, with the undesirable side effect of tea such as those set out above being eliminated or reduced, which comprises the steps of providing an effective dosage of tea and an effective dosage of a sulfur-containing amino acid, and orally ingesting the effective dosages of tea and sulfur-containing amino acids, wherein the ingested effective dosages result in providing advantageous properties of tea with the undesirable side effects of tea being eliminated or reduced.

The tea preferably is green tea, oolong tea, black tea, or a combination thereof.

The sulfur-containing amino acid preferably is methionine (e.g., L-methionine, DL-methionine), cysteine, cystine, taurine, or a combination thereof.

Optionally, folic acid (folate), vitamin B12, or a combination thereof, may be added to the formulations.

The ranges for the tea powder preferably are from about 30 mg. to about 1.0 gm for relieving headaches and for reducing or stabilizing blood pressure. However, the amount of tea may extend outside these ranges. In formulations with more than about 0.5 grams of tea, the benefit of alleviating or preventing angina pectoris has been observed.

The ranges for the sulfur-containing amino acid preferably are from about 0.3 grams–1.5 grams. However, the amount of sulfur-containing amino acid may extend outside these ranges.

The ranges for vitamin B6 preferably are from about 20 mg to about 100 mg. 50 mg of vitamin B6 is preferred.

The ranges for the vitamin C preferably are from about 0.3 grams to about 1.0 gram. 500 mg of vitamin C is preferred.

The ranges for folic acid (folate) preferably are from about 200 micrograms to about 600 micrograms. 400 micrograms of folic acid (folate) is preferred.

The ranges for vitamin B12 preferably are from about 100 micrograms to about 200 micrograms. 150 micrograms of vitamin B12 is preferred.

A composition comprising about 0.6 to about 0.7 grams of tea, about 0.6 to about 0.7 grams of sulfur-containing amino acid, and about 50 mg. of vitamin B6 is a particularly preferred embodiment of the invention.

I now turn to the examples of the invention, all ingredients being by weight unless indicated otherwise.

EXAMPLE 1

A 62 year old patient suffering from headaches began drinking tea in an effort to relieve the headaches. The patient reported that his headaches subsided after drinking tea for five days, but the tea was irritating his stomach. The patient discontinued drinking tea due to the stomach irritation, and the patient reported that the headaches returned. The patient then ingested the combination of 0.6 grams of dry ground-up green tea and 0.7 grams of DL-methionine at bed time each night. The patient reported that his headaches soon disappeared without the recurrence of stomach irritation. The patient further reported that he began to sleep comfortably for five to six hours every night and woke up each morning without a headache.

The following examples 2–9 further illustrate the invention. The ingredients of the formulation in these examples are all by weight unless indicated otherwise. In each example, the undesirable side effects of tea, such as insomnia, dizziness, heart palpitations, excessive urination, stomach upset, stomach pain, nausea, vomiting, and constipation, do not occur after ingesting the inventive composition.

EXAMPLE 2

A composition for relieving headaches and symptoms of angina, which also has the benefits of keeping hair healthy and skin healthy, was formulated according to the invention wherein 0.6 grams of green tea powder, 0.7 grams DL-methionine and 50 mg. of vitamin B-6 were ingested concurrently by an individual. The individual repeated the course of ingestion with the same amounts of the composition each night for a 2 ½ years period of time. During the time duration which the person was ingesting the composition, symptoms of angina pectoris subsided. The composition also has use for reducing or eliminating headaches and migraine headaches, and improving the healthy properties of skin and hair (such as color, texture and appearance).

EXAMPLE 3

Example 1 is repeated, however, in place of the dry, ground-up green tea, oolong tea is used. The results and benefits obtained are the same as those obtained when using the composition of Example 1.

EXAMPLE 4

Example 1 is repeated, however, in place of the dry, ground-up green tea, dry, ground-up black tea is used. The results and benefits obtained are the same as those obtained when using the composition of Example 1.

EXAMPLE 5

Example 1 is repeated, however, in place of the dry, ground-up green tea, a mixture containing dry, ground-up green tea, oolong tea and black tea is used. The results and benefits obtained are the same as those obtained when using the composition of Example 1.

EXAMPLE 6

A formulation for lowering blood pressure and improving the healthy properties of skin and hair (such as color, texture, and appearance), is taken by a patient who ingests a combination of 50 mg of dry ground up green tea, 1.0 gram DL-methionine, 0.5 grams vitamin C, and 50 mg vitamin B6. The composition is taken once or twice daily.

EXAMPLE 7

Example 2 is repeated, however, in place of the dry, ground-up green tea, oolong tea is used. The results and benefits obtained are the same as those obtained when using the composition of Example 2.

EXAMPLE 8

Example 2 is repeated, however, in place of the dry, ground-up green tea, dry, ground-up black tea is used. The results and benefits obtained are the same as those obtained when using the composition of Example 2.

EXAMPLE 9

Example 2 is repeated, however, in place of the dry, ground-up green tea, a mixture containing dry, ground-up green tea, oolong tea and black tea is used. The results and benefits obtained are the same as those obtained when using the composition of Example 2.

EXAMPLE 10

A formulation for caffeine sensitive or caffeine allergic individuals, or for individuals who do not like tea, is illustrated in this example. This formulation helps lower or stabilize blood pressure, helps promote healthy hair, and helps provide a healthy shine (such as color, texture, and appearance) to hair. The formulation comprises a combination of 1.0 gram DL-methionine, 0.5 grams vitamin C, and 50 mg vitamin B6, which is ingested by the patient once or twice daily, resulting in stablizing or reducing the blood pressure of the patient and providing healthy hair as well as a healthy shine to the hair of the patient.

Improved results may be observed by ingestion of the combinations according to the invention, such as those illustrated in the examples provided herein. To further enhance the effects of the compositions of the present invention, cutting out salty food, meat products and dairy products from a person's diet and increasing green leafy vegetables and soy bean products into a person's diet further enhance the desired results. If bad cholesterol is lowered by an individual through adjusting dietary intake, the results produced by the invention may be further enhanced.

The above examples show the use of about 0.6 grams of a ground-up tea. It will be understood that the tea, such as green tea, oolong tea, black tea or a mixture thereof, may be provided in ranges of amounts, as mentioned above. The examples above can be carried out with these amounts to offer the same benefits and results obtained heretofore. Similarly, the sulfur-containing amino acid, which has been specified as 0.7 grams in the above examples, will be understood to vary in accordance with the ranges set forth herein, and provide the results consistent with the invention, affording the benefits herein reported with the use of the compositions of the invention described herein.

The method according to the present invention, includes providing an effective first dosage of (i) tea, or (ii) tea and vitamin B6, or (iii) tea, vitamin B6, and vitamin C, or (iv) vitamins C and B6, in combination with an effective second dosage of a sulfur-containing amino acid, and orally ingesting the dosages. The components of the dosages are preferably ingested simultaneously, and it is particularly preferred to provide a unitary dosage such as in a tablet form which contains the components of the first and second dosages so that these components are ingested simultaneously. The method described herein may be used in accordance with the above inventive compositions which may be delivered to a human, orally, in accordance with the steps of the method of the invention, as disclosed.

ADVANTAGES

In addition to the advantage of providing the advantageous properties of tea with the undesirable side effects of tea being eliminated or reduced, the invention provides additional advantages. For instance, ingesting the inventive compositions disclosed herein appears to strengthen the ingestor's hair, as well as darkening it.

Additionally, ingesting the inventive compositions according to the invention, in addition to assisting to stabilize or reduce blood pressure, enhances the healthiness of hair and skin. Those who have ingested the inventive compositions over time have noticed the fading of age spots and the delay of skin wrinkling.

The inventive compositions may also be ingested without upsetting one's stomach.

In formulations of the invention with more than about 0.5 grams of tea, the benefit of alleviating or preventing angina pectoris has been observed.

What is claimed is:

1. A composition for alleviating angina pectoris, delaying wrinkling of skin, delaying greying of hair, and relieving headaches, consisting of
   a dry ground-up tea, and
   an added sulfur-containing amino acid.

2. The composition of claim 1, the tea being green tea, oolong tea, black tea, or a combination thereof.

3. The composition of claim 1, the sulfur-containing amino acid being L- or DL-methionine, cysteine, cystine, taurine, or a combination thereof.

4. The composition of claim 1, the tea being present in an amount of about 0.3 grams to about 1.0 gram.

5. The composition of claim 1, the sulfur-containing amino acid being present in an amount of about 0.3 grams to 1.5 grams.

6. The composition of claim 1, the tea being green tea, oolong tea, black tea, or a combination thereof,
   the tea being present in an amount of about 0.3 grams to about 1.0 gram,
   the sulfur-containing amino acid being L- or DL-methionine, cysteine, cystine, taurine, or a combination thereof, and
   the sulfur containing amino acid being present in a range of about 0.3 grams to 1.5 grams.

7. The composition of claim 1, the dry ground-up tea being in a powder form or a granular form.

8. A unit dosage for alleviating angina pectoris, and/or delaying wrinkling of skin, and/or delaying greying of hair, and/or relieving headaches, comprising:
   a dry ground-up tea, and
   a sulfur-containing amino acid,
   the tea being present in an amount of about 0.3 grams to about 1.0 gram,
   the tea being in a range of about 16% to about 77% by weight of the composition,
   the sulfur-containing amino acid being present in a range of about 0.3 grams to about 1.5 grams, and
   the sulfur-containing amino acid being in a range of about 23% to about 83% by weight of the composition.

9. The composition of claim 8, the tea being green tea, oolong tea, black tea, or a combination thereof.

10. The composition of claim 8, the sulfur-containing amino acid being L- or DL-methionine, cysteine, cystine, taurine, or a combination thereof.

11. The composition of claim 8, the tea being present in an amount of about 0.6 grams.

12. The composition of claim 8, the tea being present in an amount of about 0.7 grams.

13. The composition of claim 8, the sulfur-containing amino acid being present in an amount of about 0.6 grams.

14. The composition of claim 8, the sulfur-containing amino acid being present in an amount of about 0.7 grams.

15. The composition of claim 8, the tea comprising green tea, oolong tea, black tea, or a combination thereof,
   the tea being present in an amount of about 0.6 grams,
   the sulfur-containing amino acid being L- or DL-methionine, cysteine, cystine, taurine, or a combination thereof,
   the sulfur-containing amino acid being present in an amount of about 0.7 grams, and
   the composition further including vitamin B6,
   the vitamin B6 being present in an amount of about 50 mg.

16. The composition of claim 8, further including vitamin B6.

17. The composition of claim 16, further including vitamin C.

18. The composition of claim 8, further including folic acid.

19. The composition of claim 16, further including folic acid.

20. The composition of claim 17, further including folic acid.

21. The composition of claim 8, further including vitamin B12.

22. The composition of claim 16, further including vitamin B12.

23. The composition of claim 17, further including vitamin B12.

24. The composition of claim 18, further including vitamin B12.

25. The composition of claim 19, further including vitamin B12.

26. The composition of claim 20, further including vitamin B12.

27. The composition of claim 18, the sulfer-containing amino acid being L-cystine.

28. The composition of claim 8, the dry groud-up tea being in a powder form or a granular form.

29. The composition of claim 17, where in the vitamin C is present in the amount of about 0.3 grams to about 1.0 grams.

30. The composition of claim 16, where in the vitamin B6 is present in the amount of about 20 mg to about 100 mg.

* * * * *